United States Patent
Hakozaki et al.

(10) Patent No.: US 11,013,678 B2
(45) Date of Patent: May 25, 2021

(54) MULTI-COMPONENT SKIN CARE PRODUCT

(71) Applicant: The Procter & Gamble Company, Cincinnati, OH (US)

(72) Inventors: Tomohiro Hakozaki, Cincinnati, OH (US); John Erich Oblong, Loveland, OH (US); Jesus Velazquez, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/196,997

(22) Filed: Jun. 29, 2016

(65) Prior Publication Data

US 2016/0374919 A1    Dec. 29, 2016

Related U.S. Application Data

(60) Provisional application No. 62/186,033, filed on Jun. 29, 2015.

(51) Int. Cl.
*A61K 8/60* (2006.01)
*A61K 8/04* (2006.01)
(Continued)

(52) U.S. Cl.
CPC .............. *A61K 8/602* (2013.01); *A61K 8/044* (2013.01); *A61K 8/06* (2013.01); *A61K 31/706* (2013.01);
(Continued)

(58) Field of Classification Search
None
See application file for complete search history.

(56) References Cited

U.S. PATENT DOCUMENTS

| 5,053,230 | A | 10/1991 | Gazzani |
| 5,833,998 | A | 11/1998 | Biedermann et al. |

(Continued)

FOREIGN PATENT DOCUMENTS

| CN | 102 871 863 | | 4/2014 |
| EP | 1493430 | B1 | 11/2009 |

(Continued)

OTHER PUBLICATIONS

U.S. Appl. No. 15/141,976, filed Apr. 29, 2016, Tomohiro NMN Hakozaki.

(Continued)

*Primary Examiner* — Robert A Wax
*Assistant Examiner* — Quanlong N Truong
(74) *Attorney, Agent, or Firm* — John G. Powell

(57) ABSTRACT

A skin care product is provided. The skin care product includes a multi-component skin care composition disposed in a multi-chamber container. The multi-component skin care composition includes an aqueous carrier component and a nicotinamide riboside component disposed in separate chambers, which prevents these components from contacting one another prior to use. The aqueous carrier component and the nicotinamide riboside component can be separated from one another by one or more fluid impermeable dividing members and/or activatable elements, which upon activation enable contact between the aqueous carrier component and nicotinamide riboside component.

19 Claims, 7 Drawing Sheets

(51) Int. Cl.
*A61K 31/706* (2006.01)
*A61Q 19/00* (2006.01)
*A61K 8/06* (2006.01)
*A61Q 19/02* (2006.01)
*B65D 25/04* (2006.01)
*B65D 43/02* (2006.01)
*B65D 51/28* (2006.01)
*B65D 81/32* (2006.01)

(52) U.S. Cl.
CPC ............ *A61Q 19/00* (2013.01); *A61Q 19/02* (2013.01); *B65D 25/04* (2013.01); *B65D 43/02* (2013.01); *B65D 51/2821* (2013.01); *B65D 81/32* (2013.01); *A61K 2800/87* (2013.01); *A61K 2800/882* (2013.01)

(56) References Cited

U.S. PATENT DOCUMENTS

| | | | |
|---|---|---|---|
| 5,968,528 | A | 10/1999 | Deckner et al. |
| H0002013 | H | 2/2002 | Boyd et al. |
| 8,106,184 | B2 | 1/2012 | Sauve |
| 8,197,807 | B2 | 6/2012 | Brenner |
| 8,383,086 | B2 | 2/2013 | Brenner |
| 8,933,217 | B2 | 1/2015 | Rinsch et al. |
| 8,999,923 | B2 | 4/2015 | Cao et al. |
| 2002/0022052 | A1 | 2/2002 | Dransfield |
| 2002/0193321 | A1* | 12/2002 | Vishnupad ............ A61K 8/8147 514/29 |
| 2003/0032617 | A1 | 2/2003 | Harel et al. |
| 2005/0123487 | A1* | 6/2005 | Spadini .................... A61K 8/22 424/47 |
| 2005/0176677 | A1 | 8/2005 | Dal Farra et al. |
| 2005/0227327 | A1 | 10/2005 | Brenner |
| 2005/0267023 | A1 | 12/2005 | Sinclair |
| 2006/0040851 | A1 | 2/2006 | Ghosh |
| 2006/0229265 | A1 | 10/2006 | Milburn |
| 2007/0027095 | A1 | 2/2007 | Brenner |
| 2007/0231288 | A1 | 10/2007 | Arnaud et al. |
| 2008/0025932 | A1 | 1/2008 | Bissett et al. |
| 2008/0312169 | A1 | 12/2008 | Johnson et al. |
| 2009/0186093 | A1 | 7/2009 | Liu et al. |
| 2009/0196942 | A1 | 8/2009 | Goyarts |
| 2010/0015072 | A1* | 1/2010 | Polla ...................... A61K 8/675 424/60 |
| 2010/0040608 | A1 | 2/2010 | Wahren-Herlenius |
| 2011/0101021 | A1* | 5/2011 | Greer ................. B65D 81/3211 222/1 |
| 2011/0262560 | A1 | 10/2011 | Dabe et al. |
| 2012/0003168 | A1 | 1/2012 | Lyga et al. |
| 2012/0022013 | A1 | 1/2012 | Sinclair |
| 2012/0121534 | A1 | 5/2012 | Thorel et al. |
| 2012/0172584 | A1* | 7/2012 | Sauve .................. C07H 19/048 536/28.1 |
| 2012/0225050 | A1 | 9/2012 | Knight et al. |
| 2013/0319449 | A1 | 12/2013 | Xavier et al. |
| 2014/0065099 | A1 | 3/2014 | Alvarez et al. |
| 2014/0090660 | A1 | 4/2014 | Xavier et al. |
| 2014/0127332 | A1 | 5/2014 | Bitler |
| 2014/0170195 | A1 | 6/2014 | Fassih et al. |
| 2014/0190507 | A9 | 7/2014 | Xavier et al. |
| 2014/0288052 | A1* | 9/2014 | Blum ...................... A61P 43/00 514/210.21 |
| 2014/0328775 | A1 | 11/2014 | Laughlin, II |
| 2015/0229711 | A1 | 8/2015 | Krueger |
| 2016/0077080 | A1 | 3/2016 | Laughlin, II |
| 2016/0235646 | A1 | 8/2016 | Shah et al. |
| 2016/0250241 | A1 | 9/2016 | Deren-Lewis et al. |
| 2016/0317418 | A1 | 11/2016 | Hakozaki et al. |
| 2016/0317419 | A1 | 11/2016 | Hakozaki et al. |
| 2016/0317420 | A1 | 11/2016 | Hakozaki et al. |
| 2016/0374908 | A1 | 12/2016 | Hakozaki et al. |
| 2016/0374918 | A1 | 12/2016 | Dihora et al. |
| 2017/0121746 | A1 | 5/2017 | Velasquez et al. |
| 2017/0196795 | A1 | 7/2017 | Hakozaki |

FOREIGN PATENT DOCUMENTS

| | | | |
|---|---|---|---|
| EP | 3040065 A1 | 7/2016 | |
| FR | 2845596 A1 | 4/2004 | |
| FR | 2975295 A1 | 11/2012 | |
| GB | 2472379 A | 2/2011 | |
| WO | WO0071093 A1 | 11/2000 | |
| WO | WO2006/127987 | 11/2006 | |
| WO | WO2011074143 A1 | 6/2011 | |
| WO | WO2014152016 A1 | 9/2014 | |
| WO | WO2015061512 A1 | 4/2015 | |
| WO | WO-2015066382 A1 * | 5/2015 | ........... A61K 31/706 |
| WO | WO2015/186114 | 12/2015 | |
| WO | WO2016034519 A1 | 3/2016 | |
| WO | WO2016188691 A1 | 12/2016 | |

OTHER PUBLICATIONS

U.S. Appl. No. 15/141,994, filed Apr. 29, 2016, Tomohiro NMN Hakozaki.
U.S. Appl. No. 15/142,044, filed Apr. 29, 2016, Tomohiro NMN Hakozaki.
U.S. Appl. No. 15/196,924, filed Jun. 29, 2016, Jiten Odhavji Dihora.
U.S. Appl. No. 15/196,967, filed Jun. 29, 2016, Tomohiro NMN Hakozaki.
U.S. Appl. No. 15/296,083, filed Oct. 18, 2016, Juan Esteban Velasquez.
Ebanks Jody P et al: "Mechanisms regulating skin pigmentation: the rise and fall of complexion coloration.", International Journal of Molecular Sciences Sep. 2009, vol. 10, No. 9, Sep. 2009.
Ferrza, J. et al. "Kinetic α-Deuterium Isotope Effects for Enzymatic and Nonenzymatic Hydrolysis of Nicotinamide-β-Riboside" Archives of Biochemistry and Biophysics vol. 191, No. 2, December pp. 431-436, 1978, 6 pages.
Oppenheimer, N. "NAD Hydrolysis: Chemical and Enzymatic Mechanisms" Molecular and Cellular Biochemistry 138: 245-251, 1994.
Hakozaki T et al: "The effect of niacinamide on reducing cutaneous pigmentation and suppression of melanosome transfer", British Journal of Dermatology, Oxford : Wiley-Blackwell, UK, vol. 147. No. 1, Jul. 1, 2002.
International Search Report PCT/US2016/029943; dated Jul. 1, 2016; 19 pages.
International Search Report PCT/US2016/029945; dated Jun. 27, 2016; 15 pages.
International Search Report PCT/US2016/039924; dated Aug. 26, 2016; 11 pages.
International Search Report PCT/US2016/039925; dated Aug. 25, 2016; 11 pages.
Sinthupoom Nujarin et al: "Nicotinic acid and derivatives as multifunctional pharmacophores for medical applications", European Food Research and Technology, Springer Verlag. Heidelberg. DE. vol. 240, No. 1. Oct. 29, 2014 (Oct. 29, 2014). pp. 1-17.
U.S. Appl. No. 62/155,672, filed May 1, 2015, Tomohiro NMN Hakozaki.
A.B. Kimball et al., Reduction in the appearance of facial hyperpigmentation after use of moisturizers with a combination of topical niacinamide and N-acetyl glucosamine: results of a randomized, double-blind, vehicle-controlled trial, British Journal of Dermatology 2010, vol. 162, No. 2, pp. 435-441.
All Office Actions, U.S. Appl. No. 15/141,976.
All Office Actions, U.S. Appl. No. 15/141,994.
All Office Actions, U.S. Appl. No. 15/142,044.
All Office Actions, U.S. Appl. No. 15/196,924.
All Office Actions, U.S. Appl. No. 15/196,967.
International Search Report and Written Opinion of the International Searching Authority, PCT/US2017/012786, dated Mar. 20, 2017, 13 pages.
JPO, Well-known Technique.
Rovito et al., Nicotinamide preferentially protects glycolysis in dermal fibroblasts under oxidative stress conditions, British Journal of Dermatology, vol. 169, Suppl. 2, pp. 15-24, Mar. 4, 2013.

(56) References Cited

OTHER PUBLICATIONS

International Search Report and Written Opinion PCT/US2016/029951 dated Aug. 23, 2016, 11 pages.
International Search Report and Written Opinion PCT/US2016/039926 dated Aug. 22, 2016, 11 pages.

* cited by examiner

MULTI-COMPONENT SKIN CARE PRODUCT

FIELD

The present disclosure is directed generally to a skin care product in a dual chamber container. More specifically, the present disclosure is directed to an aqueous skin care composition comprising nicotinamide riboside and water, wherein the NR and water are not in fluid communication with one another prior to use.

BACKGROUND

Skin conditions include some of the most common disorders treated in the developing world, and treating such conditions has led to a booming skin care industry, which generates billions of dollars in sales each year. Different skin conditions are associated with widely varied triggers, biological mechanisms, environmental factors, and clinical manifestations. For example, as people age, intrinsic factors related to the biochemical changes within the skin typically result in visible signs of skin aging such as wrinkling and other forms of roughness (including increased pore size, flaking and skin lines) and/or uneven skin pigmentation (e.g., age spots or melasma). In some instances, lifestyle choices and exposure to the environment may allow extrinsic factors such as ultraviolet radiation, pollution (e.g., engine exhaust, cigarette smoke, smog), wind, heat, low humidity, harsh surfactants, abrasives, and the like to damage the skin, leading to undesirable skin appearance. As a result, a multitude of cosmetic skin care products have been developed that contain skin care agents tailored to treat common skin conditions.

An example of skin care agents known for use in skin care products are Vitamin $B_3$ compounds such as niacin and its derivatives. U.S. Pat. No. 4,096,240 refers to niacin as effective in skin lightening. U.S. Pat. No. 8,106,184 discloses treating skin or epithelial cells with a nicotinoyl riboside or derivative compound that increases the level of intracellular nicotinamide adenine dinucleotide NAD+ to treat skin afflictions or skin conditions such as disorders or diseases associated with or caused by inflammation, sun damage or natural aging. U.S. Publication No. 2005/0267023 discloses methods and compositions for modulating the life span of a cell or its resistance to stress, for example, by contacting the cell with nicotinamide riboside to stimulate the NAD+ salvage pathway in the cell. PCT Pub. No. WO 2015/066382 ("Deren-Lewis") relates to methods of using nicotinamide riboside to promote the increase of intracellular levels of (NAD+) in cells and tissues for improving cell and tissue survival. Deren-Lewis discloses the use of topical nicotinamide riboside compositions for treating a variety of skin conditions by modulating the NAD+ pathway.

It has recently been found that nicotinamide riboside ("NR") may be a particularly suitable skin care agent. But incorporating NR into an aqueous cosmetic composition such as an emulsified skin care composition can be problematic. Many cosmetic compositions include water, and NR tends to hydrolyze in the presence of water. The hydrolysis of NR in skin care compositions has not been appreciated before now. The rate and amount of hydrolysis depends on the amount of water present, the length of time the NR is exposed to the water and the temperature. See, "Kinetic a-Deuterium Isotope Effects for Enzymatic and Nonenzymatic Hydrolysis of Nicotinamide-β-Riboside" by Ferraz, et al., Department of Chemistry, Indiana University, Archives of Biochemistry and Biophysics, Vol. 191, No. 2, pp. 431-436, 1978. Thus, by the time a consumer is ready to use an NR-containing cosmetic product, the NR may be substantially degraded or no longer present. In some instances, it may even be desirable to incorporate NR into ingestible compositions such as beverages, which typically include a substantial amount of water. In these instances, it is particularly important to minimize or prevent hydrolysis of NR in the composition.

Accordingly, it would be desirable to inhibit and/or prevent hydrolysis of the NR in an aqueous composition by separating the NR from the water-containing portions of the composition prior to use or dispensing.

SUMMARY

A skin care product is provided. In one aspect, the skin care product comprise a multi-chambered container comprising an outer wall that defines an interior storage space, and at least two storage chambers disposed in the interior storage space, wherein the storage chamber are separated from one another by at least one water-impermeable dividing member; and a multi-component skin care composition comprising a nicotinamide riboside (NR) component disposed in a first chamber of the multi-chamber container and an aqueous carrier component disposed in a second chamber of the multi-chamber container. In some instances, the composition may encompass one or more of the following features: the NR component comprises nicotinamide riboside chloride; the NR component comprises NR dissolved in a miscible solvent; the NR component comprises NR dispersed in an immiscible fluid; a porous carrier with the NR disposed thereon; the porous carrier is selected from zeolites, precipitated silicates, microspheres and combinations thereof; at least one additional skin care agent; the aqueous carrier component is a water-in-oil or oil-in-water emulsion; the multi-chambered container comprises a mixing chamber, and the NR component and aqueous carrier component are mixed together in the mixing chamber prior to being dispensed; the container dispenses an effective amount of NR; the effective amount of NR provides a skin lightening benefit.

In another aspect, the skin care product comprises a container comprising a body, an interior storage space disposed in the body, an opening that enable a user to access a fluent composition contained in the interior storage space, a lid removably joined to the body for covering the opening and an NR storage space, wherein the interior storage space and the NR storage space are physically separated from one another (e.g., by a water impermeable barrier); and a multi-component skin care composition comprising an aqueous carrier component disposed in the interior storage space of the container and an NR component disposed in the NR storage space. In some instances, the composition may encompass one or more of the following features: the NR storage space is disposed in a portion of the lid; the NR storage space is a discrete element joined to at least one of the body and the lid; the NR storage space is a self-contained capsule or pouch; the self-contained capsule or pouch is formed from a material that is soluble in the aqueous carrier component of the skin care composition; the capsule or pouch is removably joined to the container; the NR storage space includes an activatable element that, when activated, enables the NR component to be contacted with the aqueous component of the multi-component skin care composition; the activatable element comprises a rupturable membrane disposed over a recessed portion of the lid; the activatable element comprises a removable membrane or seal covering an opening in the container.

DETAILED DESCRIPTION

Figure 1:
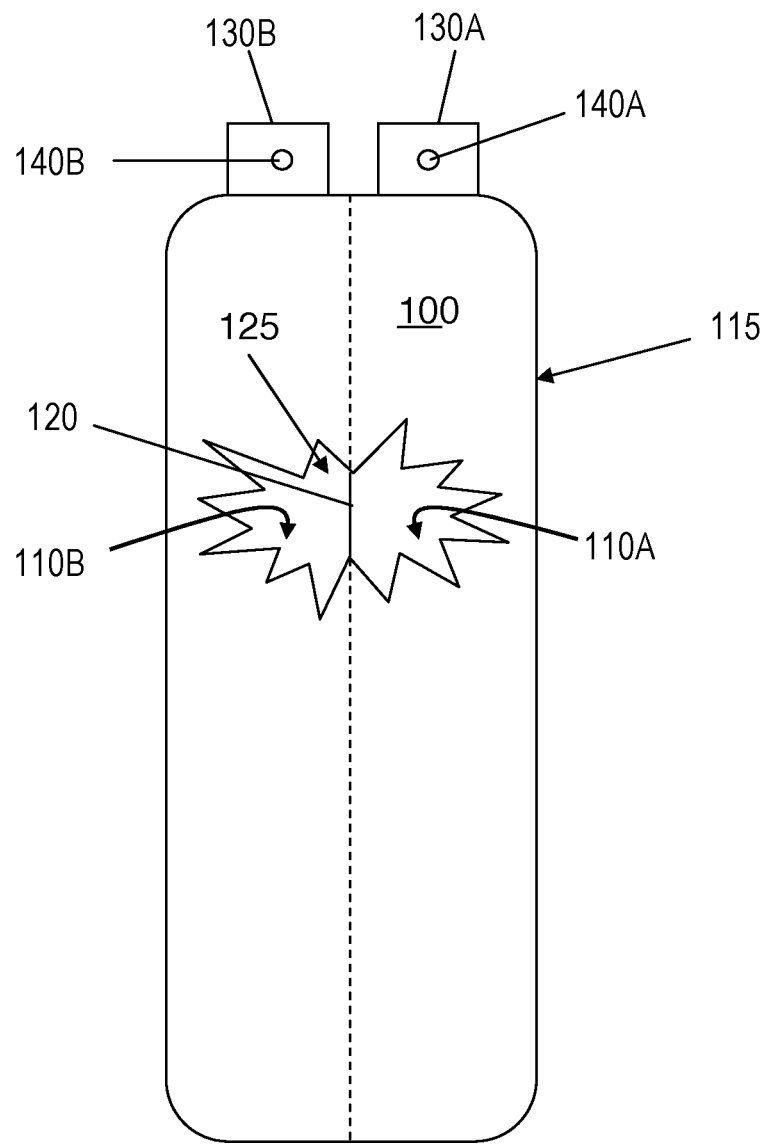
FIG. 1 is an illustration showing a partial cutaway plan view of a multi-chamber container.

The susceptibility of NR to hydrolysis limits its usefulness in cosmetic skin care compositions, many of which tend to be aqueous. Thus, In order to reduce and/or prevent the hydrolysis of NR in an aqueous composition, the NR containing component and water containing component of the composition are stored in separate portions of the container.

Materials, features, structures and/or characteristics may be combined in any suitable manner across different instances, and materials, features, structures and/or characteristics may be omitted or substituted from what is described. Thus, embodiments and instances described herein may comprise or be combinable with elements or components of other embodiments and/or instances despite not being expressly exemplified in combination, unless otherwise stated or an incompatibility is stated.

All percentages are by weight of the cosmetic composition or encapsulated particles, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The cosmetic compositions described herein can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"About," as used herein, modifies a particular value, by referring to a range equal to the particular value, plus or minus twenty percent (+/−20%).

"Apply" or "application", as used in reference to a composition, means to apply or spread the compositions of the present invention onto a human skin surface such as the epidermis.

"Aqueous" refers to materials or compositions that contain at least 20% water.

"Cosmetic" means providing a desired visual effect on an area of the human body. The visual cosmetic effect may be temporary, semi-permanent, or permanent.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe ("GRAS") by the U.S. Food and Drug Administration, food additives, and materials used in non-cosmetic consumer products including over-the-counter medications. The compositions herein may optionally include one or more cosmetic agents in addition to nicotinamide riboside. In some embodiments, cosmetic agents may be incorporated in a cosmetic composition comprising a dermatologically acceptable carrier suitable for topical application to skin.

"Dispenser" refers to a structure configured to dispense fluent product(s) from inside a container to the environment outside of the container.

"Disposed" means an element is positioned in a particular place relative to another element.

"Effective amount" means the amount of nicotinamide riboside sufficient to provide the desired skin benefit (e.g., improve the appearance of a hyperpigmented spot) over the course of a treatment period. For example, in some instances, an effective of NR is an amount sufficient to provide a skin lightening benefit (e.g., improve the appearance of a hyperpigmented spot) over the course of a treatment period.

"Fluid impermeable" refers to a material through which fluids cannot pass absent catastrophic failure (e.g., rupturing, tearing, breaking, melting or dissolving) of the material.

"Generally recognized as safe" or "GRAS" refers to a material that complies with Sections 201(s) and 409 of the Federal Food, Drug, and Cosmetic Act, and the U.S. Food and Drug Administration's ("FDA") implementing regulations set forth in 21 CFR 170.3 and 21 CFR 170.30, which require the premarket review and approval by the FDA of any use of a food substance, unless the substance is generally recognized, among qualified experts, as having been adequately shown to be safe under the conditions of its intended use either through scientific procedures or, for a substance used in food before 1958, through experience based on common use in food.

"Joined" refers to the condition where a first component is affixed, or connected, to a second component either directly; or indirectly, where the first component is affixed, or connected, to an intermediate component which in turn is affixed, or connected, to the second component. The joined condition between the first component and the second component is intended to remain for the life of the product. Components are considered "removably joined" if the components may be detached and separated from each other without unintended destruction or gross deformation of either component. "Reattachably joined" refers to components that can be rejoined at least once after being separated from one another without significant degradation of their structural or functional properties.

"Product chamber" means an enclosable or enclosed three-dimensional space configured to receive and directly contain one or more fluent product(s), wherein that space is defined by one or more materials that form a barrier that prevents the fluent product(s) from escaping the product volume. "Directly containing" means the fluent products come into contact with the material(s) that define the three-dimensional space and there is no intermediate material or container to prevent such contact.

"Mixing chamber" refers to a portion of a container that is configured to receive two or more fluent products from two or more product chambers and mix the products together.

"Skin care agent" means a cosmetic agent for regulating and/or improving a skin condition. Some nonlimiting examples of regulating and/or improving a skin condition include improving skin appearance and/or feel by providing a smoother, more even appearance and/or feel; increasing the thickness of one or more layers of the skin; improving the elasticity or resiliency of the skin; improving the firmness of the skin; reducing the oily, shiny, and/or dull appearance of skin; improving the hydration status or moisturization of the skin; improving the appearance of fine lines and/or wrinkles; improving skin exfoliation or desquamation; plumping the skin; improving skin barrier properties; improving skin tone; reducing the appearance of spots, redness or skin blotches; and/or improving the brightness, radiancy, or translucency of skin. Examples of skin care agents include moisturizing agents, conditioning agents, anti-microbials, humectants, vitamins, peptides and peptide derivatives, sugar amines, sunscreens, oil control agents, particulates, flavonoid compounds, hair growth regulators, antioxidants, phytosterols, protease inhibitors, tyrosinase inhibitors, anti-inflammatory agents, and mixtures thereof. Skin care agents may incorporated in topical compositions for direct application to a target skin area, or incorporated into an ingestible composition such as a beverage and delivered to a target skin portion via the digestive and circulatory systems of the body.

"Treatment period," as used herein means the length of time and/or frequency that the encapsulated cosmetic agent is used. The treatment period may be a predetermined length of time and/or frequency.

"Water insoluble" refers to a material that does not readily dissolve in water (e.g., has a water solubility at 25-50° C. of less than 200 millimoles/liter, less than 100 millimoles/liter, less than 50 millimoles/liter or even less than 10 millimoles/liter).

Skin Care Product

The skin care product herein is a fluent, multi-component skin care composition disposed in a multi-chambered container. The fluent, multi-component skin care composition includes a nicotinamide riboside component disposed in a first product chamber of the multi-chamber container and an aqueous carrier component disposed in a second product chamber of the multi-chamber container. The multi-component skin care compositions herein may, optionally, include one or more additional components (e.g., 2, 3, 4 or more) disposed in one or more product chambers of the multi-chamber container, which may be the same as or different from the product chambers containing the NR component and/or aqueous component.

It may be desirable to configure the skin care product herein to dispense a cosmetic composition that includes an effective amount of NR. For example, suitable methods for metering the amount of product dispensed from a container are known in the art and may be employed to dispense a skin care composition that includes from about 0.05%, 0.5%, 1%, 2%, 3%, 4% or 5% to about 20%, 15%, 10%, 8% or 6% by weight of the cosmetic composition of NR.

Nicotinamide riboside (CAS No. 1341-23-7) generally takes the form of a dry powder and has the formula:

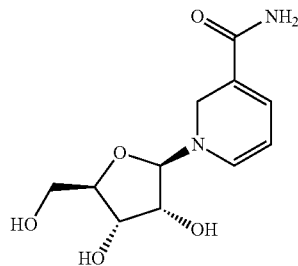 [SMILES: NC(=O)C1=CC=CN([C@@H]2O[C@H](CO)[C@@H](O)[C@H]2O)C1]

Some examples of nicotinamide riboside and its methods of manufacture are described in U.S. Pat. No. 8,106,184. As used herein, the term "nicotinamide riboside" includes derivatives of nicotinamide riboside (e.g., nicotinamide riboside chloride). Nicotinamide riboside may be obtained from ChromaDex, Inc., Irvine, Calif.

In some instances, the skin care compositions herein include an amount of NR sufficient to reduce the amount of HMGB1 protein released from keratinocytes, for example, by at least 10%, 15%, 20%, 25%, 30%, 35%, 40%, 45%, 50%, 55%, 60%, 65%, 70%, 75%, 80%, 85%, 90%, 95% or even 100%. It may be particularly desirable for the effective amount of NR to reduce HMGB1 protein levels and/or activity in stressed keratinocytes (i.e., keratinocytes exposed to a stressor such as ultraviolet radiation) to pre-stress levels or below, which could result in a reduction of greater than 100%. HMGB1 protein level can be determined by using a conventional HMGB1 ELISA kit (e.g., the High Mobility Group Box 1 Protein (HMGB1) ELISA Kit available from IBL International as REF #ST51011) according to the manufacturer's instructions.

Reducing HMGB1 protein levels, and thus dendrite stimulation caused by HMGB1 protein may improve the appearance of hyperpigmented spots and/or overall skin tone. In some instances, the improvement may correspond to a positive change in L* value (i.e., a ΔL* value that is greater than 0, but typically less than 100) when the nicotinamide riboside is applied during a treatment period and/or at the end of a treatment period. In some instances, the ΔL* value may be from 0.1 to 10, from 0.2 to 5, from 0.3 to 3. Additionally or alternatively, the improvement in appearance may correspond to a reduction in Spot Area Fraction of at least 2% (e.g., from 2% to 100%, from 5% to 70%, from 10% to 40%, from 15% to 25%).

In some instances, the NR component of the multi-component skin care composition herein may include NR powder particles dissolved in a miscible fluid. Some non-limiting examples of solvents that can dissolve NR are 3-methyl isoxazole, acetanilide, succinic anhydride, pyridazine, 1-methyl imidazole, salicylaldehyde, tetrahydrofurfuryl alcohol, 2-pyrolidone, 2-pyrrolidinone, isoxazole, dimethyl sulfone, tetramethylene sulfone, thiazole, thiourea, b-propiolactone, ethylene cyanohydrin, dimethyl sulfoxide, dimethyl sulfoxide, 1,3-triazole, diethylenetriamine, diethylenetriamine, dimethyl formamide, n,n-dimethylformamide, 2-chloropropenoic acid, acetonecyanhydrin, shellac, polyethylene oxide 4000, sorbitol and combinations of these.

In some instances, the NR component of the multi-component skin care compositions herein may include NR powder particles dispersed or suspended in an immiscible solvent. Some non-limiting examples of such immiscible fluids are mono, di- and tri-esters of C4-C24 fatty acids and glycerin; fatty acid esters of polyglycerol oligomers; poly-alphaolefins, butyl oleate, hydrogenated castor oil, sucrose benzoate, dodecanoic acid, palmitic acid, stearic acid, octadecanoic acid, monoester with 1,2,3-propanetriol; dodecanoic acid, pentyl ester; octanoic acid, nonyl ester; pentadecanoic acid, ethyl ester; hexadecanoic acid, methyl ester; dodecanoic acid, 4-methylphenyl ester; dodecanoic acid, 3-methylbutyl ester; tetradecanoic acid, 1-methylethyl ester; hexadecanoic acid; 1-phenanthrenecarboxylic acid, hexarose; butyl oleate; hydrogenated castor oil; isopropyl myristate; castor oil; mineral oil; isoparaffin; capryllic triglyceride; soybean oil; vegetable oil; geranyl palmitate; silicones; polydimethylsiloxane; heptadecane; isododecane; perfume raw materials with a Calculated log P ("C log P") of greater than 5 using the C LOG P program available from Daylight Chemical Information Systems Inc., Irvine, Calif.

In some instances, solubilized NR can be loaded into porous carrier particles such as zeolites, precipitated silicas or lattice-network microspheres, and then dissolved or dispersed in a suitable non-aqueous liquid. In these instances, the NR is generally contained within the pores or lattice of the porous carrier particles.

The NR component may, optionally, include one or more additional ingredients known for use in skin care compositions, provided the optional components do not unacceptably alter the desired benefits of the skin care composition. The optional components, when present, may be included at an amount of about 50%, 40%, 30%, 20%, 10%, 5%, or 3%, by weight of the composition, for example, at least about 0.001%, 0.01%, 0.1%, 0.2%, 0.5%, or 1%, by weight of the composition. Suitable ranges include any combination of the lower and upper limits including suitable ranges from about 0.1% to about 50%; from about 0.2% to about 20%; or from about 1% to about 10%, by weight of the composition. The optional components, when incorporated into the composition, should be non-aqueous and suitable for use in contact with human skin tissue without undue toxicity, incompatibility, instability, allergic response, and the like. Nonlimiting examples of optional components include skin anti-aging agents, skin tone agents, anti-inflammatory agents, anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives such as those described in U.S. Publication Nos. 2006/0275237 and 2004/0175347.

Aqueous Carrier

The multi-component skin care composition herein includes an aqueous carrier component, which provides a suitable matrix to store and deliver the NR and/or other optional ingredients (e.g., skin care agents). When the skin care composition herein is intended for topical application to skin, the aqueous carrier should be "dermatologically acceptable," which means it is suitable for topical application to keratinous tissue, has good aesthetic properties, is compatible with the actives in the composition, and will not cause any unreasonable safety or toxicity concerns. In some embodiments, the aqueous carrier component may include one or more optional components known for use in cosmetic compositions, provided the optional components do not unacceptably alter the desired benefits of the present skin care composition. The optional components, when present, may be included at an amount of about 50%, 40%, 30%, 20%, 10%, 5%, or 3%, by weight of the composition, for example, at least about 0.001%, 0.01%, 0.1%, 0.2%, 0.5%, or 1%, by weight of the composition. Suitable ranges include any combination of the lower and upper limits including suitable ranges from about 0.1% to about 50%; from about 0.2% to about 20%; or from about 1% to about 10%, by weight of the composition. The optional components, when incorporated into the composition, should be suitable for use in contact with human skin tissue without undue toxicity, incompatibility, instability, allergic response, and the like. Nonlimiting examples of optional components include skin anti-aging agents, skin tone agents, anti-inflammatory agents, anti-acne actives, desquamation actives, anti-cellulite agents, chelating agents, flavonoids, tanning active, non-vitamin antioxidants and radical scavengers, hair growth regulators, anti-wrinkle actives, anti-atrophy actives, minerals, phytosterols and/or plant hormones, N-acyl amino acid compounds, antimicrobial or antifungal actives, and other useful skin care actives such as those described in U.S. Publication Nos. 2006/0275237 and 2004/0175347.

The aqueous carrier can be in a wide variety of forms such as a simple solution, an emulsion or a gel. In a particularly suitable example, the aqueous carrier is in the form of an emulsion with a continuous aqueous phase (e.g., oil-in-water and water-in-oil-in-water) or a continuous oil phase (e.g., water-in-oil and oil-in-water-in-oil). The aqueous phase includes water, and may include any optional water soluble ingredients. The oil phase may include silicone oils, non-silicone oils such as hydrocarbon oils, esters, ethers, and the like, and mixtures thereof.

Emulsions may further comprise an emulsifier. The composition may comprise any suitable percentage of emulsifier to sufficiently emulsify the carrier. Suitable weight ranges include from about 0.1% to about 10% or about 0.2% to about 5% of an emulsifier, based on the weight of the composition. Emulsifiers may be nonionic, anionic or cationic. Suitable emulsifiers are disclosed in, for example, U.S. Pat. Nos. 3,755,560, 4,421,769, and McCutcheon's Detergents and Emulsifiers, North American Edition, pages 317-324 (1986). Suitable emulsions may have a wide range of viscosities, depending on the desired product form.

The carrier may further comprise a thickening agent as are well known in the art to provide compositions having a suitable viscosity and rheological character.

Multi-Chamber Container

The multi-chamber container herein is configured to receive, contain and dispense a fluent, multi-component, skin care composition. The multi-chamber container generally includes an outer wall that defines an interior storage space, at least two product chambers (e.g., 2, 3, 4, 5, 6, 7, 8, 9 or 10) disposed in the interior storage space, at least one water impermeable dividing member (e.g., 1, 2, 3, 4, 5, 6, 7, 8, 9, 10) that separates the product chambers, a dispenser and, optionally, one or more mixing chambers. The present containers may be disposable or reusable, flexible or rigid, and may be made from any suitable material known for making such containers (e.g., molded plastic bottles, formed films, glass jars, metal cans, cardboard boxes). The product chambers, optional mixing chamber(s) and dispenser may be configured to receive, store and/or dispense a fluent product of any volume desired. In some instances, the container may be formed by joining 2 or more product chambers together to form a unitary container. Additionally or alternatively, some or all of the various container elements may be formed as integral parts of the container and not as separate elements. It is to be appreciated that any of the product chambers and/or mixing chambers can be configured with any number of any kind of dispenser configured in any suitable manner known in the art.

The product chambers are configured to receive and store the aqueous carrier component and the NR component of the multi-component skin care composition, and any other optional ingredients desired. In some instances, the product chambers are defined by the outer wall of the container and the fluid impermeable dividing member that divides the interior storage space of the container into discrete chambers. Additionally or alternatively, the product chambers may be self-contained, for example, by forming or inserting expandable bladders into the interior storage space. In this example, the expandable bladders may be formed from a plastic, elastic or plastoelastic material capable of preventing the fluent material stored therein from escaping before it is dispensed by a user. In some instances, the product chambers may be arranged in a side-by-side configuration, in which the product chambers are generally parallel to one another in the lengthwise direction of the container. In some instances, the product chambers may be arranged in a stacked configuration in the lengthwise direction of the container.

In some instances, the containers may include an optional mixing chamber. The mixing chamber, when included, provides one or more flow channels in fluid communication with two or more product chambers. The mixing chamber combines the fluent produces from the product chambers together before the point of dispensing, thus allowing products from multiple product chambers to be mixed together prior to being dispensed. The mixing chamber may be disposed between the product chambers and the dispenser, or it may be a unitary or integral part of the dispenser. The mixing chamber may utilize any suitable means of mixing fluent compositions known in the art for mixing the various fluent components in the present skin care composition. For example, the mixing chamber may create a tortuous flow channel between the various product chambers and the dispenser opening. In this example, the discrete streams of fluent product enter a common tortuous flow channel where they are mixed together prior exiting the dispenser opening. In another example, the mixing chamber can be configured as an intersection between two or more flow channels in liquid communication with multiple product chambers. In this example, the fluent product from the multiple product chambers enters the mixing chamber via multiple flow channels and exit through a single flow channel.

The multi-chamber container includes one or more dividing members that provide a fluid impermeable barrier between the various product chambers, thereby preventing the fluent products contained therein from coming into contact with one another prior to dispensing. In particular, the dividing member prevents the water from the aqueous carrier component of the composition from contacting the NR from the NR component of the composition. The dividing member may be rigid or flexible and may be formed from any suitable material that is not solubilized or broken down by the ingredients in the skin care composition.

The present container includes a dispenser for dispensing the fluent compositions in the product chambers to the external environment. The dispenser is not particularly limited and may include any suitable dispenser known in the art for dispensing a fluent composition. Some non-limiting examples of dispensers are push-pull type dispensers, dispensers with a flip-top cap, dispensers with a cap (e.g., screw-on or snap-on type cap), rotatable type dispensers, dip tube type dispensers, pump type dispensers, trigger spray type dispensers, straw dispensers, flip up straw dispensers, dosing dispensers. In some instances, the dispenser includes multiple dispensers providing multiple flow channels in fluid communication with multiple product volumes, wherein said flow channels remain separate until the point of dispensing, thus allowing simultaneous but separate dispensing of multiple fluent product streams. As further examples, a dispenser can utilize one or more valves and/or dispensing mechanisms disclosed in the art, such as those disclosed in U.S. Publication No. 2003/0096068 and U.S. Pat. Nos. 4,988,016 and 7,207,717. The dispenser may be incorporated into the container either directly, or in combination with one or more other materials or structures (such as a fitment), or in any suitable way known in the art. In some instances, the dispenser may be configured for both dispensing and filling. When multiple dispensers are used, they may have the same or different flow rates.

In some instances, the container herein may include a lid disposed over the dispenser to reduce or prevent the undesirable evaporation of water or other volatile components from the skin care composition. The lid may be removable and/or reattachable, and may be made from any suitable known in the art for making lids.

FIGS. 1 to 9 illustrate various examples of multi-chamber containers for storing the multi-components skin care compositions herein. FIG. 1 shows a container 100 that has an outer wall 115 defining an interior storage space 125. The interior storage space 125 contains first and second product chambers 110A and 110B. Dividing member 120 creates a water impermeable barrier between the first and second product chambers 110A and 110B. The container 100 includes a first and second dispenser 130A and 130B in fluid communication with the first and second product chambers 110A and 110B, respectively. The first and second dispensers 130A and 130B each include a dispenser opening 140A and 140B, respectively, which are configured to dispense the fluent product contained in the product chambers 110A and 110B.

Figure 2:
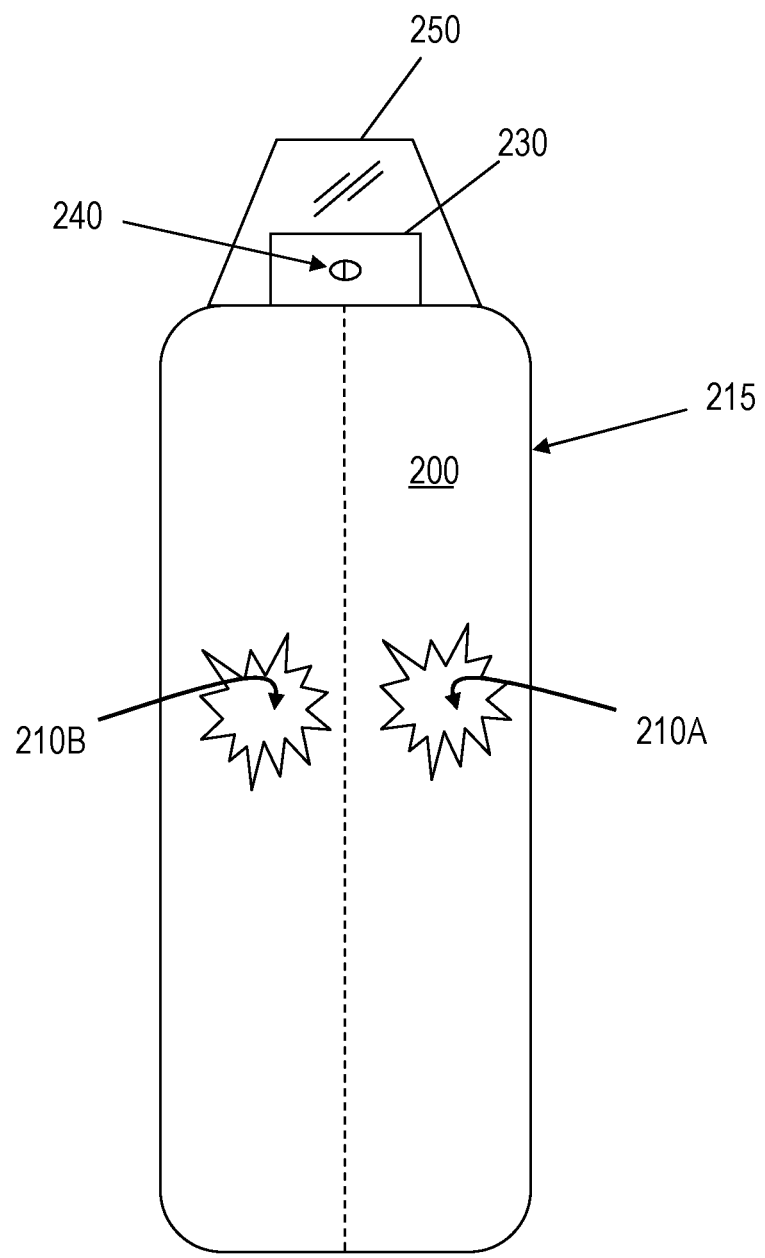
FIG. 2 is an illustration showing a partial cutaway plan view of a multi-chamber container.

FIG. 2 shows a container 200 that includes an outer wall 215 defining an interior storage space (not shown), which contains first and second product chambers 210A and 210B. The container 200 includes a single dispenser 230 in liquid communication with both product chambers 210A and 210B. The dispenser 230 includes a bifurcated dispenser opening 240. The bifurcated opening 240 enables metered dispensing of two product streams simultaneously. The container 200 may optionally include a lid 250. The lid 250 in this example is transparent, but it is to be appreciated that the lid 250 may be opaque or translucent, as desired.

Figure 3:
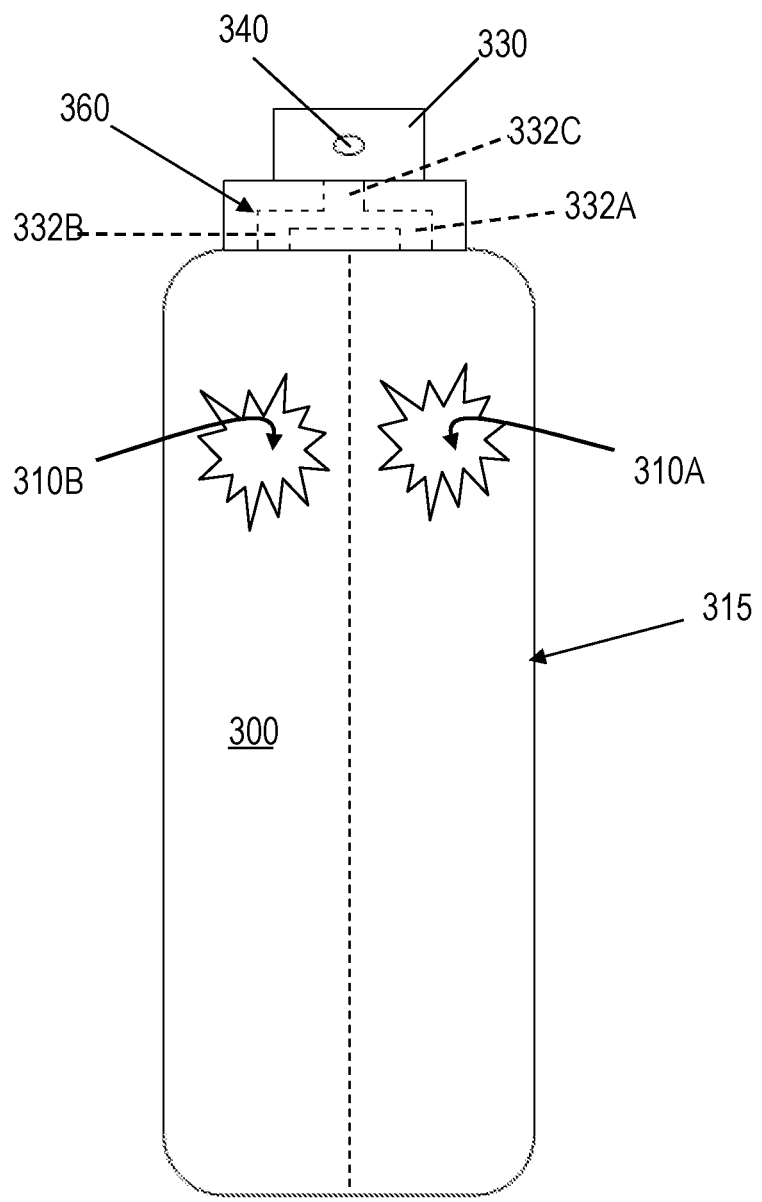
FIG. 3 is an illustration showing a partial cutaway plan view of a multi-chamber container.

FIG. 3 shows a container 300 that includes an outer wall 315 defining an interior storage space (not shown), which contains first and second product chambers 310A and 310B. The container 300 includes a single dispenser 330 in liquid communication with both product chambers 310A and 310B. Disposed between the dispenser 330 and the product chambers 310A and 310B is a mixing chamber 360. The mixing chamber 360 is in fluid communication with the first and second product chambers 310A and 310B via first and second flow paths 332A and 332B, respectively. The mixing chamber 360 combines the fluent product streams from the first and second flow paths 332A and 332B into a single product stream in third flow path 332C, which is in fluid communication with dispensing opening 340.

Figure 4:
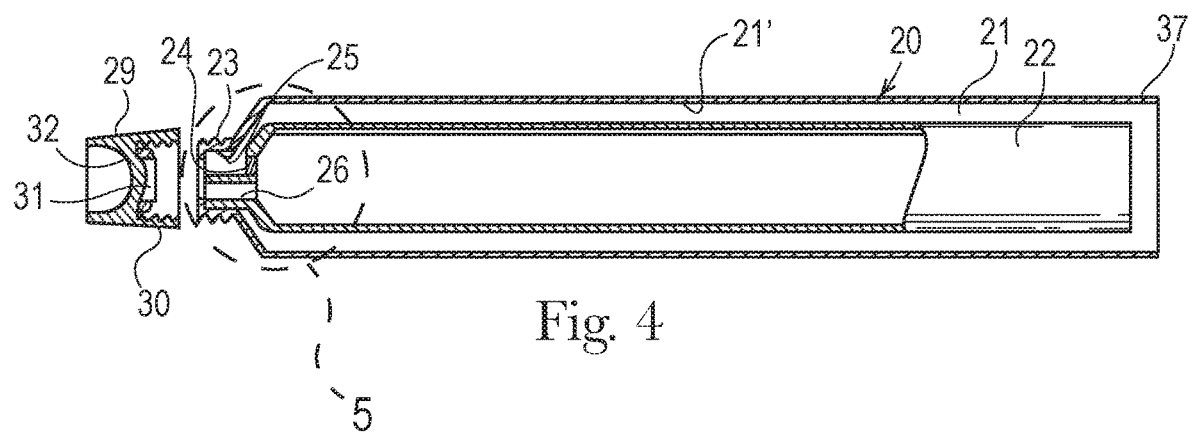
FIG. 4 is an illustration showing a partial cutaway plan view of a multi-chamber container.
Figure 5:
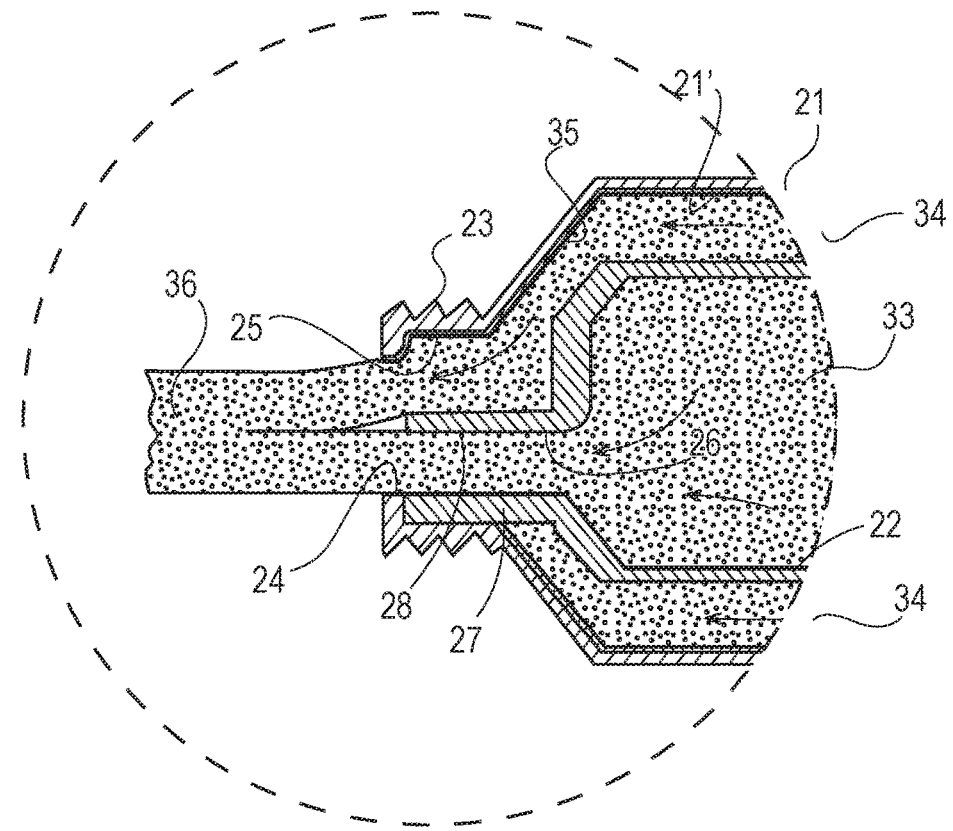
FIG. 5 is a magnified view of the dispensing end of the multi-chamber container of FIG. 4.

FIGS. 4-8 illustrate examples of a container in a "tube-in-tube" configuration. The container 20 is made up of an outer tube 21, which may include an optional inert coating 21', an inner tube 22, a threaded end portion 23 of the outer tube 21, an aperture 24 of the outer tube 21, a sub-aperture 25 in the outer tube 21; an aperture 26 of the inner tube 22 including a neck 27 and a partition or wall 23, a cap or common closure means 29 including threads 30, a boss 31 and optionally a gasket 32. The container 20 may also include a passageway 35 between the two tubes and an extension 37 of the outer tube 21 beyond the inner tube 22. In use, as illustrated in FIG. 5, the fluent products in the inner tube 33 and the outer tube 34 (separated by the partition or wall 28) are merged into the single stream 36.

Figure 6:
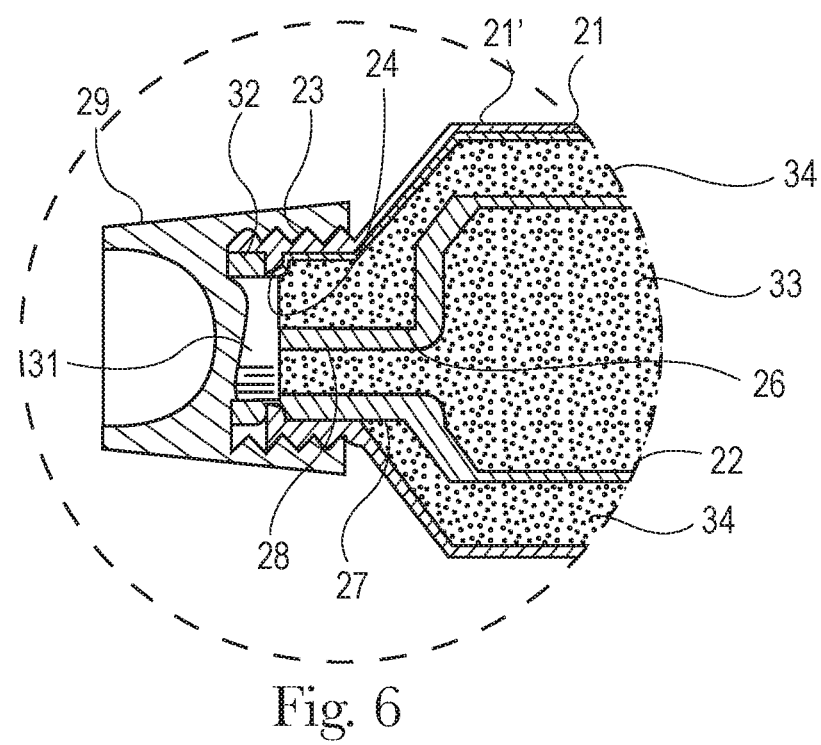
FIG. 6 is a magnified view of the dispensing end of the multi-chamber container of FIG. 4 with a lid joined to the dispensing end of the container.
Figure 7:
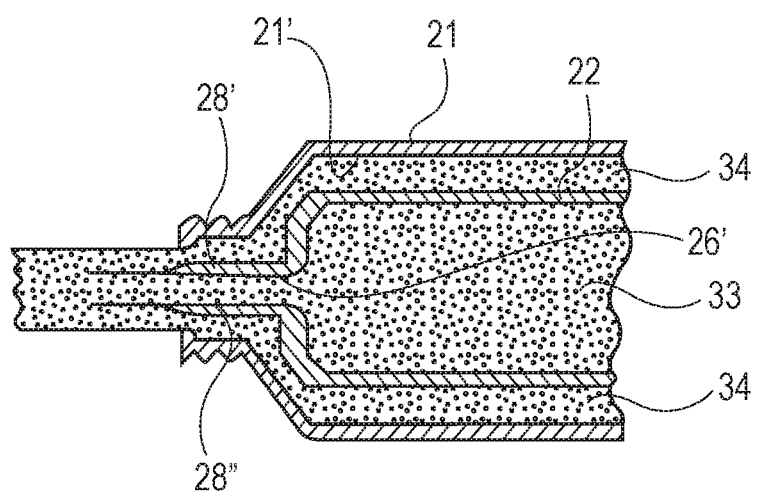
FIG. 7 is an alternate embodiment of the container of FIG. 4.
Figure 8:
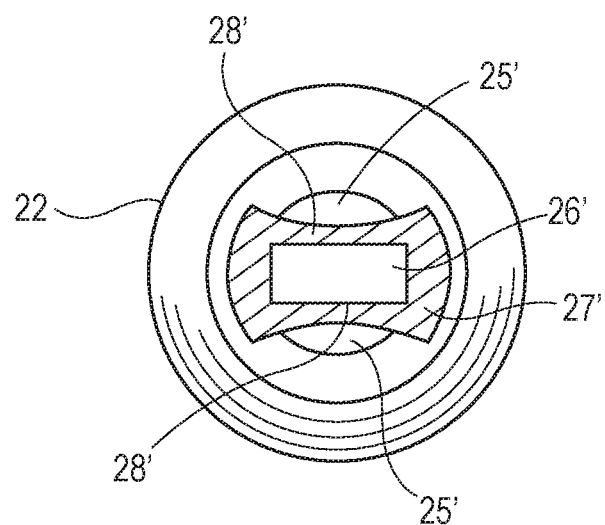
FIG. 8. is an end view of the container of FIG. 7.

FIGS. 7 and 8 illustrate the tube-in-tube container 20 of FIGS. 4 to 6, except that the inner tube 22 has a single aperture 26 and two walls 28' and 28"connected by neck portions 27'. The outer tube 21 has two apertures 25'.

Figure 9:
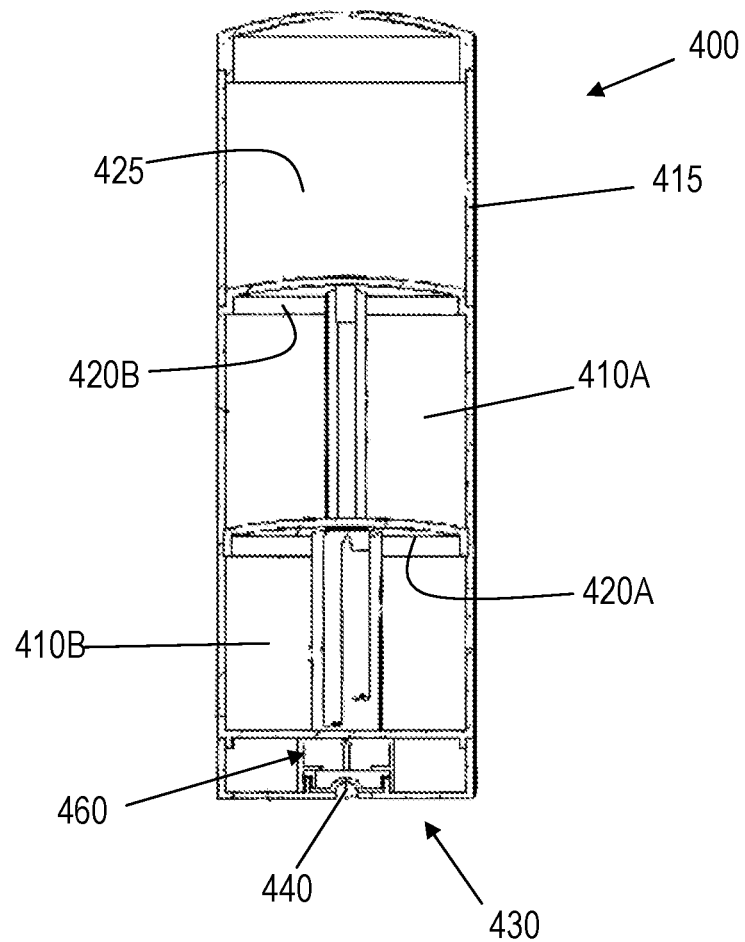
FIG. 9 is a cross-section view of a multi-chamber container.

FIG. 9 illustrates an example of a container 400 in a "stacked" configuration. The container 400 includes an outer wall 415 defining an interior storage space 425. The interior storage includes first and second product chambers 410A and 410B, separated from one another and from other portions of the interior storage space 425 by movable dividing members 420A and 420B. The movable dividing members 420A and 420B may be moved by an actuator (not shown) operable by user to force the products in one or both products chambers out of the dispenser 430, for example, using a conventional plunger-type assembly. The dispenser 430 is in liquid communication with the product storage chambers 410A and 410B, and the container 400 may optionally include a mixing chamber 460 to mix the fluent product from the product chambers 410A and 410B prior to dispensing through dispensing opening 440.

In some instances, the multi-component skin care composition may be in the form of a fluent oral composition intended to be ingested by a human (i.e., a beverage). In these instances, the container herein is configured to receive, store and dispense beverages. Such containers are generally known in the art (e.g., bottles, jars, cans, boxes, pouches and the like). The beverage containers herein include a main body that has an interior storage space generally defined by a fluid imperious outer wall, which may be rigid or flexible and formed from any suitable material known in the art (e.g., plastic, glass, cardboard, and aluminum). The interior storage space typically contains the aqueous carrier component of the multi-component skin care composition, which may be in the form of a beverage. The container includes an opening, which allows a user to access the beverage stored within the container, and, optionally, a lid to cover the opening. The lid may provide or help provide a liquid and/or moisture impervious barrier between the interior storage space and the external environment. The lid may be removably and, optionally, reattachably joined to the main body of the container by any suitable means known in the art (e.g., screw-top, snap-on, flip-top and the like). The container may also include optional additional elements such as a membrane or seal to cover the opening in the container, which may help to prevent or reduce fluid and/or vapor loss from the beverage.

The beverage container also includes an NR storage space for separably storing the NR component of the skin care composition such that the NR component does not contact the aqueous component or any other source of water prior to use. In some instances, the NR storage space may be a discrete, self-contained element such as a capsule or pouch joined to a portion of the container (e.g., the lid or the body) by any suitable means known in the art (e.g., adhesive, melt bonding). For example, the NR storage space may be a plastic pouch, which can be opened by a user and the NR component poured into the aqueous carrier component of the skin care composition. In another example, the NR storage space may be a capsule or the like formed from a GRAS material that dissolves in the aqueous carrier component when placed therein, thereby releasing the NR component into the beverage.

In some instances, the NR storage space may be an integral or unitary part of another element of the container, which is activatable by a user. In some instances, activation of the activatable element can cause the NR component to be added directly to the beverage without the need for further action from the user. Alternatively, the user may be required to take further action after the activatable portion is activated (e.g., shaking the beverage or additional manipulation of the container or a portion thereof). The activatable element may be activated by any suitable means known in the art (e.g., removing, puncturing, rupturing, tearing, or dissolving the activatable element by shaking the container or twisting or otherwise manipulating the lid, body or other element of the container). In some instances, the NR component may be disposed in a recessed portion of the lid, such as the portion of the lid that typically fits over the mouth of a conventional beverage jar or bottle. In this example, the lid may include an activatable fluid-impermeable membrane or seal joined thereto that covers at least a portion of the recessed portion of the lid (i.e., the portion containing the NR component). Alternatively or additionally, an activatable fluid impermeable membrane or seal may be placed over the opening in the container to prevent the aqueous component from prematurely contacting the NR component. Continuing with the example, when the activatable membrane and/or seal is activated by user, it enables the NR component to contact the aqueous carrier component.

Some additional non-limiting examples of multi-chamber containers and methods of making the same are disclosed in U.S. Pat. Nos. 2,933,610; 5,921,540; 6,223,943; 6,347,726; 7,617,950; 7,976,234; and U.S. Publication 2011/0101021.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin care product, comprising:
a multi-chambered container comprising an outer wall that defines an interior storage space and at least two product storage chambers disposed in the interior storage space, wherein the product storage chambers are separated from one another by at least one water-impermeable dividing member; and
a multi-component skin care composition comprising a nicotinamide riboside (NR) component disposed in at least one of the product storage chambers and an aqueous carrier component disposed in a different product storage chamber, wherein the NR component is free of water, and wherein the NR component and the aqueous carrier component are combined prior to being dispensed from the container.

2. The skin care product of claim 1, wherein the NR component comprises nicotinamide riboside chloride.

3. The skin care product of claim 1, wherein the NR component comprises NR dissolved in a solvent capable of dissolving the NR at 25° C. and 1 atmosphere of pressure.

4. The skin care product of claim 1, wherein the NR component comprises NR dispersed in a fluid that is incapable of dissolving the NR at 25° C. and 1 atmosphere of pressure.

5. The skin care product of claim 1, wherein the NR component comprises a porous carrier with NR disposed thereon.

6. The skin care product of claim 5, wherein the porous carrier is selected from zeolites, precipitated silicates, microspheres and combinations thereof.

7. The skin care product of claim 1, wherein the multi-component skin care composition includes at least one additional skin care agent.

8. The skin care product of claim 1, wherein the aqueous carrier component is a water-in-oil or oil-in-water emulsion.

9. The skin care product of claim 1, wherein the multi-chambered container comprises a mixing chamber, and the NR component and aqueous carrier component are mixed together in the mixing chamber prior to being dispensed.

10. The skin care product of claim 1, wherein the container dispenses an effective amount of NR.

11. The skin care product of claim 10, wherein the effective amount of NR provides a skin lightening benefit.

12. A skin care product, comprising:
a container comprising a body, an interior storage space disposed in the body, an opening that enables a user to access a fluent composition contained in the interior storage space, a lid removably joined to the body for covering the opening and a nicotinamide riboside (NR) storage space, wherein the interior storage space and the NR storage space are physically separated from one another; and
a multi-component skin care composition comprising an aqueous carrier component disposed in the interior storage space of the container and an NR component disposed in the NR storage space, wherein the NR component is free of water, and wherein the NR component and the aqueous carrier component are combined prior to being dispensed from the container.

13. The skin care product of claim 12, wherein the NR storage space is disposed in a portion of the lid.

14. The skin care product of claim 13, wherein the NR storage space is a self-contained capsule or pouch.

15. The skin care product of claim 14, wherein the self-contained capsule or pouch is formed from a material that is soluble in the aqueous carrier component of the skin care composition.

16. The skin care product of claim 14, wherein the capsule or pouch is removably joined to the container.

17. The skin care product of claim 12, wherein the NR storage space includes an activatable element that, when activated, enables the NR component to be contacted with the aqueous component of the multi-component skin care composition.

18. The skin care product of claim 17, wherein the activatable element comprises a rupturable membrane disposed over a recessed portion of the lid.

19. The skin care product of claim 17, wherein the activatable element comprises a removable membrane or seal covering an opening in the container.

* * * * *